United States Patent
Nakashima et al.

(10) Patent No.: US 9,357,942 B2
(45) Date of Patent: Jun. 7, 2016

(54) BIOSIGNAL MEASUREMENT ELECTRODE AND BIOSIGNAL MEASUREMENT APPARATUS

(71) Applicant: Sony Corporation, Tokyo (JP)

(72) Inventors: Yusaku Nakashima, Tokyo (JP); Haruhiko Soma, Tokyo (JP)

(73) Assignee: Sony Corporation, Tokyo (JP)

( * ) Notice: Subject to any disclaimer, the term of this patent is extended or adjusted under 35 U.S.C. 154(b) by 79 days.

(21) Appl. No.: 14/021,605

(22) Filed: Sep. 9, 2013

(65) Prior Publication Data

US 2014/0081116 A1    Mar. 20, 2014

(30) Foreign Application Priority Data

Sep. 14, 2012 (JP) ................................. 2012-203118

(51) Int. Cl.
*A61B 5/0478* (2006.01)
*A61B 5/0492* (2006.01)

(52) U.S. Cl.
CPC ............. *A61B 5/0478* (2013.01); *A61B 5/0492* (2013.01); *A61B 2562/125* (2013.01); *A61B 2562/14* (2013.01); *A61B 2562/168* (2013.01)

(58) Field of Classification Search
CPC ......................... A61B 5/0478; A61B 2562/168
USPC .................. 600/372, 382–384, 386.388–392, 600/395–397; 607/153
See application file for complete search history.

(56) References Cited

U.S. PATENT DOCUMENTS

| | | | | |
|---|---|---|---|---|
| 3,279,468 A * | 10/1966 | Le Vine | ......................... | 607/140 |
| 3,508,541 A * | 4/1970 | Westbrook et al. | ........... | 600/383 |
| 3,868,946 A * | 3/1975 | Hurley | ............................ | 600/392 |
| 4,033,334 A * | 7/1977 | Fletcher et al. | ............... | 600/383 |
| 4,137,909 A * | 2/1979 | Hix | ................................ | 600/392 |
| 4,805,600 A * | 2/1989 | Wess | .................. | A61B 17/2251 |
| | | | | 601/4 |
| 5,357,957 A * | 10/1994 | Itil | ........................ | A61B 5/0478 |
| | | | | 600/383 |
| 7,930,013 B2 * | 4/2011 | Ponton | .......................... | 600/383 |
| 9,113,842 B2 * | 8/2015 | Nishiyama | ........... | A61B 5/6802 |
| 2007/0238945 A1 * | 10/2007 | Delic et al. | ..................... | 600/383 |

FOREIGN PATENT DOCUMENTS

JP       2008-302089       12/2008

* cited by examiner

*Primary Examiner* — Lee S Cohen
(74) *Attorney, Agent, or Firm* — Chip Law Group (57) ABSTRACT

A biosignal measurement electrode includes a liquid retaining member, an electric plate, and a cover member. The liquid retaining member is configured to be elastically deformed and impregnated with conductive liquid, the liquid retaining member including a contact surface configured to be brought into contact with a living body surface. The electric plate is configured to be brought into contact with the conductive liquid. The cover member is configured to be elastically deformed and cover the liquid retaining member except for the contact surface.

11 Claims, 8 Drawing Sheets

BIOSIGNAL MEASUREMENT ELECTRODE AND BIOSIGNAL MEASUREMENT APPARATUS

CROSS REFERENCES TO RELATED APPLICATIONS

The present application claims priority to Japanese Priority Patent Application JP 2012-203118 filed in the Japan Patent Office on Sep. 14, 2012, the entire content of which is hereby incorporated by reference.

BACKGROUND

The present disclosure relates to a biosignal measurement electrode and a biosignal measurement apparatus that are utilized in measurement of biosignals.

A biosignal measurement electrode for measuring biosignals (various signals that can be measured from a living body such as electroencephalogram and electromyogram) is brought into contact with a living body surface and electrically connected to the living body surface to thereby acquire the biosignals. Such a biosignal measurement electrode is generally brought into contact with the living body surface via conductive liquid for ensuring an electrical connection with the living body surface.

For example, Japanese Patent Application Laid-open No. 2008-302089 (hereinafter, referred to as Patent Document 1) discloses an electrode for brain wave measurement. This electrode for brain wave measurement includes a felt impregnated with an electrolyte solution and is configured to acquire brain waves via the electrolyte solution when the felt is brought into contact with the head of a subject.

SUMMARY

However, when a measurement time is long, for example, when brain waves of a subject during sleep are continuously measured, with the electrode for brain wave measurement disclosed in Patent Document 1 or an existing electrode having a similar configuration, there is a fear that conductive liquid vapors and it becomes difficult to maintain electrical contact with a living body surface. Further, due to long-time contact of the electrode with the living body surface, pain is often produced in the living body surface. In addition, especially for brain wave measurement during sleep, an electrode that can be utilized even if the subject lies on his or her back is necessary.

In view of the above-mentioned circumstances, it is desirable to provide a biosignal measurement electrode and a biosignal measurement apparatus that are suitable for long-time measurement.

According to an embodiment of the present disclosure, there is provided a biosignal measurement electrode including a liquid retaining member, an electric plate, and a cover member.

The liquid retaining member is configured to be elastically deformed and impregnated with conductive liquid, the liquid retaining member including a contact surface configured to be brought into contact with a living body surface.

The electric plate is configured to be brought into contact with the conductive liquid.

The cover member is configured to be elastically deformed and cover the liquid retaining member except for the contact surface.

With this configuration, the liquid retaining member impregnated with the conductive liquid and the cover member covering the liquid retaining member are elastically deformed together. Thus, even if the biosignal measurement electrode is pressed against the living body surface, it is possible to reduce pain to the living body surface. Further, even if the biosignal measurement electrode causes a vibration with respect to the living body surface, the liquid retaining member and the cover member follow the living body surface and it becomes possible to continuously acquire the biosignals. In addition, the cover member covers the liquid retaining member. Thus, evaporation of the conductive liquid with which the liquid retaining member is impregnated is suppressed and it is possible to also accommodate long-time measurement of the biosignals.

The cover member may be formed of a material not transmitting the conductive liquid.

With this configuration, the conductive liquid (including vapor thereof) can be prevented from passing through the cover member to leak out of the cover member. In addition to the effect of suppressing evaporation that is obtained by covering by the cover member, it is further possible to effectively suppress evaporation of the conductive liquid.

The biosignal measurement electrode may further include a conductive member configured to be connected to the electric plate. The cover member may prevent contact of the conductive liquid with the conductive member.

The electric plate may be formed of a material (e.g., silver-silver chloride) exhibiting a small potential change even if the electric plate is brought into contact with the conductive liquid. With this, it is possible to prevent potential change noise from being caused in the biosignal. At the same time, when the conductive liquid is brought into contact with the conductive member other than the electric plate, there is a fear that potential change noise is caused. With the above-mentioned configuration, the cover member can prevent the conductive liquid from being brought into contact with the conductive member. That is, it becomes possible to prevent potential change noise from being caused in the biosignal.

The cover member may be brought into close contact with the electric plate, to thereby seal the conductive liquid by an elastic force thereof.

With this configuration, it is possible to seal the conductive liquid between the electric plate and the cover member, and to prevent the conductive liquid from being brought into contact with the conductive member other than the electric plate.

The cover member may have a bellows shape with a direction perpendicular to the contact surface being expansion and contraction directions.

With this configuration, the bellows shape can facilitate the elastic deformation of the cover member.

According to still another embodiment of the present disclosure, there is provided a biosignal measurement apparatus including a biosignal measurement electrode and equipment.

The biosignal measurement electrode includes a liquid retaining member configured to be elastically deformed and retain conductive liquid, the liquid retaining member including a contact surface configured to be brought into contact with a living body surface, an electric plate configured to be brought into the conductive liquid, and a cover member configured to be elastically deformed and cover the liquid retaining member except for the contact surface.

The equipment is configured to support the biosignal measurement electrode and cause the biosignal measurement electrode to abut against the living body surface.

With this configuration, even if the equipment is pressed against the living body surface or causes a vibration with respect to the living body surface, as described above, it is possible to effectively measure the biosignals by the biosignal measurement electrode.

The equipment may be configured to cause the biosignal measurement electrode to abut against a head of a subject, and the biosignal measurement electrode may be configured to acquire a brain wave of the subject.

As described above, without producing pain to the living body surface, the biosignal measurement electrode can continuously measure the biosignals against the vibration of the biosignal measurement electrode and suppress evaporation of the conductive liquid. Therefore, the biosignal measurement electrode can be utilized in measurement of various biosignals. In particular, the biosignal measurement electrode is suitable to be utilized as an electroencephalographic electrode.

As described above, according to the embodiments of the present disclosure, it is possible to provide a biosignal measurement electrode and a biosignal measurement apparatus that are suitable for long-time measurement.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

A biosignal measurement apparatus according to an embodiment of the present disclosure will be described. Note that it is assumed that the biosignal measurement apparatus according to this embodiment is an apparatus for brain measurement that is mounted on the head of a subject to acquire brain waves. However, the biosignal measurement apparatus according to the present disclosure is not limited to the apparatus for brain wave measurement. The present disclosure may be applied to any measurement apparatus that acquires biosignals from a living body surface.

[Configuration of Biosignal Measurement Apparatus]

Figure 1:
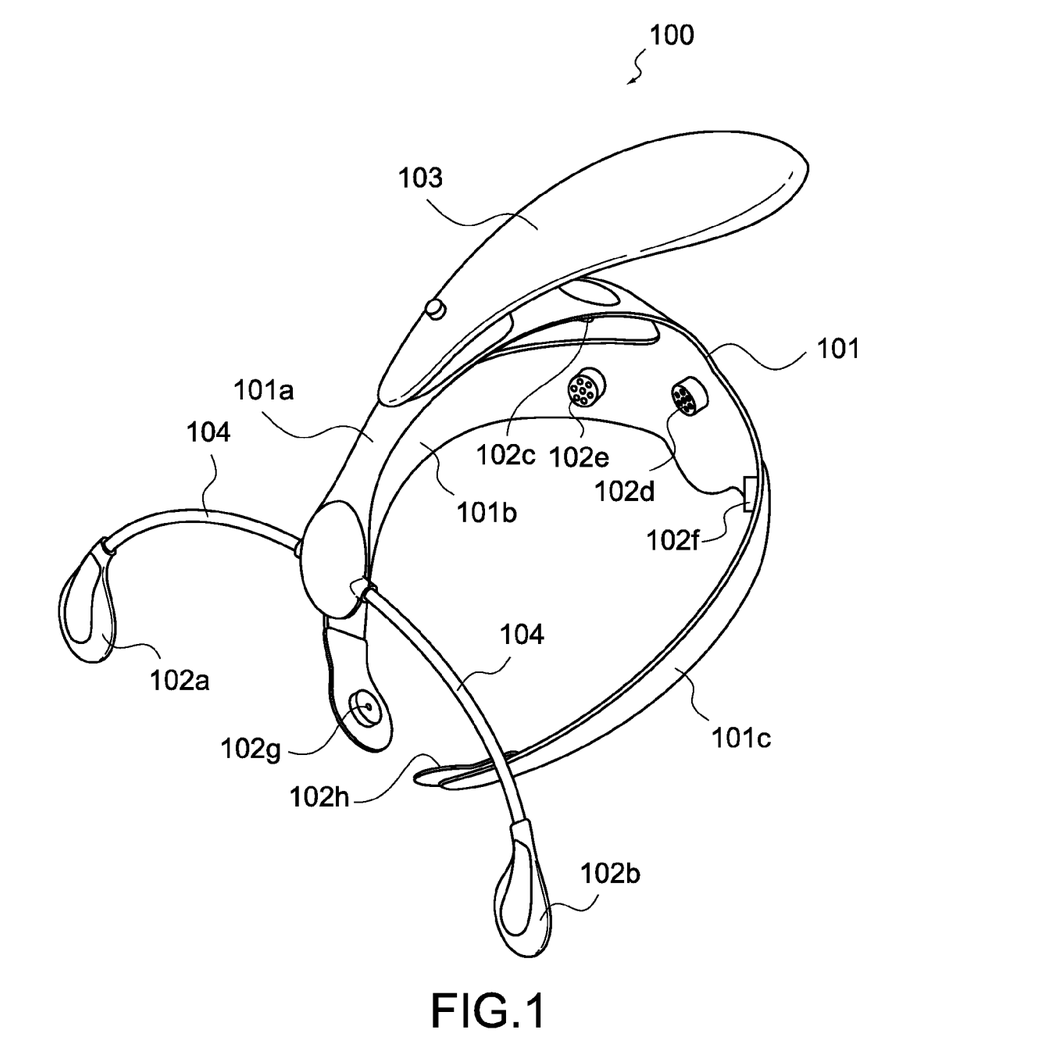
FIG. 1 is a perspective view of a biosignal measurement apparatus according to an embodiment of the present disclosure.
Figure 2:
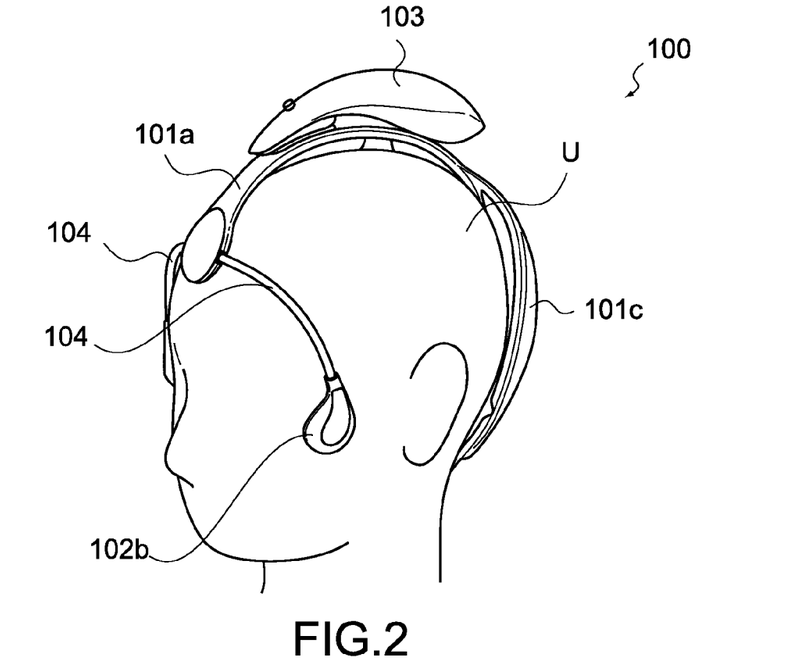
FIG. 2 is an outer appearance view of the biosignal measurement apparatus.
Figure 3:
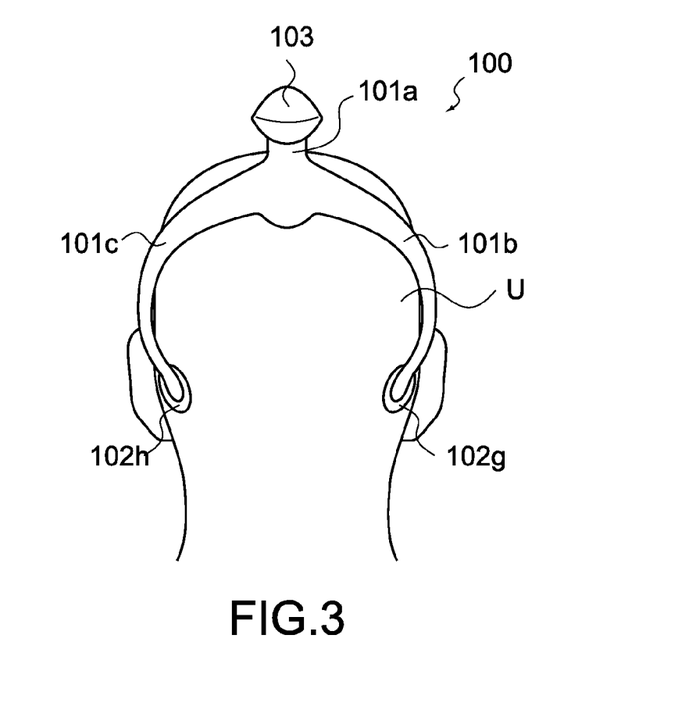
FIG. 3 is an outer appearance view of the biosignal measurement apparatus.

FIG. 1 is a perspective view of a biosignal measurement apparatus 100 according to this embodiment. FIGS. 2 and 3 are outer appearance views each showing the biosignal measurement apparatus 100 worn by a subject (in figure, subject U). FIG. 2 is a view as viewed from the left of the subject U. FIG. 3 is a view as viewed from the back of the subject U.

As shown in the figures, the biosignal measurement apparatus 100 includes equipment 101, electrodes 102a to 102h, and a signal processing unit 103. The electrodes 102a to 102h and the signal processing unit 103 are attached to the equipment 101.

The equipment 101 causes the biosignal measurement apparatus 100 to be brought into contact with the head of the subject U. Although the equipment 101 has an arbitrary configuration, favorably, the equipment 101 may be formed in a shape conforming to the head shape of the subject U and may be capable of pressing the electrodes 102a to 102h against the head with a suitable pressing force.

The electrodes 102a to 102h are electrodes for brain wave acquisition that abut against the head of the subject U to acquire brain waves of the subject U. The electrodes 102a to 102h may be a right electrooculogram (EOG) electrode 102a, a left EOG electrode 102b, a Cz measurement electrode 102c, a Pz measurement reference electrode 102d, a P4 measurement electrode 102e, a P3 measurement electrode 102f, a right reference electrode 102g, and a left reference electrode 102h, respectively. This placement (name) complies with the International 10-20 system. However, in the biosignal measurement apparatus 100 according to this embodiment, this electrode placement do not necessarily need to be adopted and different electrode placement may be adopted depending on needs.

The electrodes 102a to 102h may have an electrode structure according to the present disclosure that will be described later. Further, all the electrodes 102a to 102h do not need to have the electrode structure according to the present disclosure.

The right EOG electrode 102a and the left EOG electrode 102b are electrodes for abutting against both the temples of the subject U and measuring EOGs. The right EOG electrode 102a and the left EOG electrode 102b may be provided to arms 104 extending from the equipment 101 to the left and right temples of the subject U.

The Cz measurement electrode 102c is an electrode that is provided at a position of the equipment 101 that corresponds to the parietal region, and abuts against the parietal region of the subject U. The Pz measurement electrode 102d is an electrode that is provided at a position of the equipment 101 that corresponds to an upper portion of the occipital region, and abuts against the upper portion of the occipital region of the subject U.

The P4 measurement electrode 102e is an electrode that is provided at a position of the equipment 101 that corresponds to the upper right head region, and abuts against the upper right head region of the subject U. The P3 measurement electrode 102f is an electrode that is provided at a position of the equipment 101 that corresponds to the upper left head region, and abuts against the upper left head region of the subject U.

The Cz measurement electrode 102c, the Pz measurement electrode 102d, the P4 measurement electrode 102e, and the P3 measurement electrode 102f acquire potentials (brain waves) at their in-contact positions. Note that the number and arrangement of those electrodes 102c to 102f are arbitrary, and those measurement electrodes may be provided depending on needs of brain wave measurement.

The right reference electrode 102g is an electrode that is provided at a position of the equipment 101 that corresponds to the right mastoid region and abuts against the right mastoid region (conical protrusion located at lower rear portion of right temporal bone) of the subject U. The left reference electrode 102h is an electrode that is provided at a position of the equipment 101 that corresponds to the left mastoid region and abuts against the left mastoid region (conical protrusion located at lower rear portion of left temporal bone) of the subject U. The right reference electrode 102g and the left reference electrode 102h acquire each reference potential of the electrodes 102a to 102f.

Each of the above-mentioned electrodes 102a to 102h may be electrically connected to the signal processing unit 103 via a wiring (not shown).

As described above, the signal processing unit 103 is connected to each of the electrodes 102a to 102h, processes an output from each of the electrodes 102a to 102h, generates brain waves of the subject U at each measurement position, and outputs the generated brain waves to an external apparatus (personal computer (PC) or the like). The signal processing unit 103 may include a built-in signal processing circuit, a wireless communication circuit, a cell, and the like (not shown). The generation of the brain waves in the signal processing unit 103 can be performed by known signal processing.

[Configuration of Biosignal Measurement Electrode]

As described above, some or all of the electrodes 102a to 102h of the biosignal measurement apparatus 100 may have an electrode structure that will be described in the following. In the following description, an electrode that can be utilized for the electrodes 102a to 102h is referred to as a biosignal measurement electrode 200.

Figure 4:
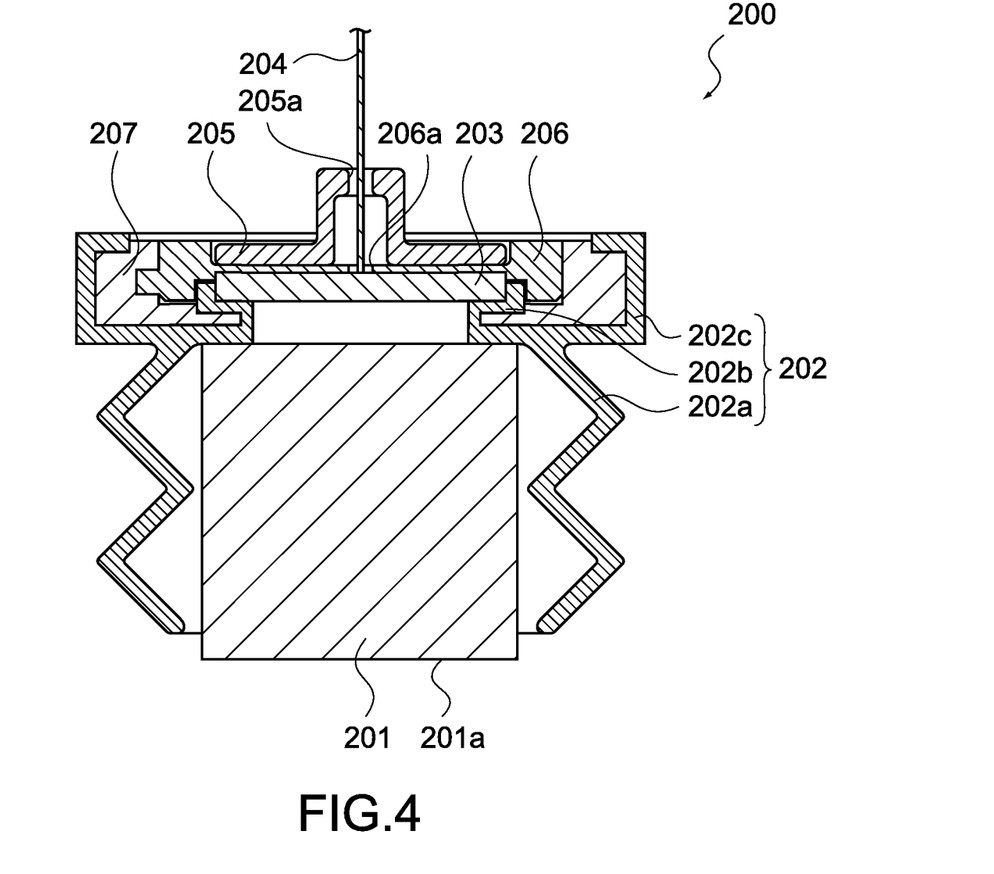
FIG. 4 is a cross-sectional view of a biosignal measurement electrode according to the embodiment of the present disclosure.
Figure 5:
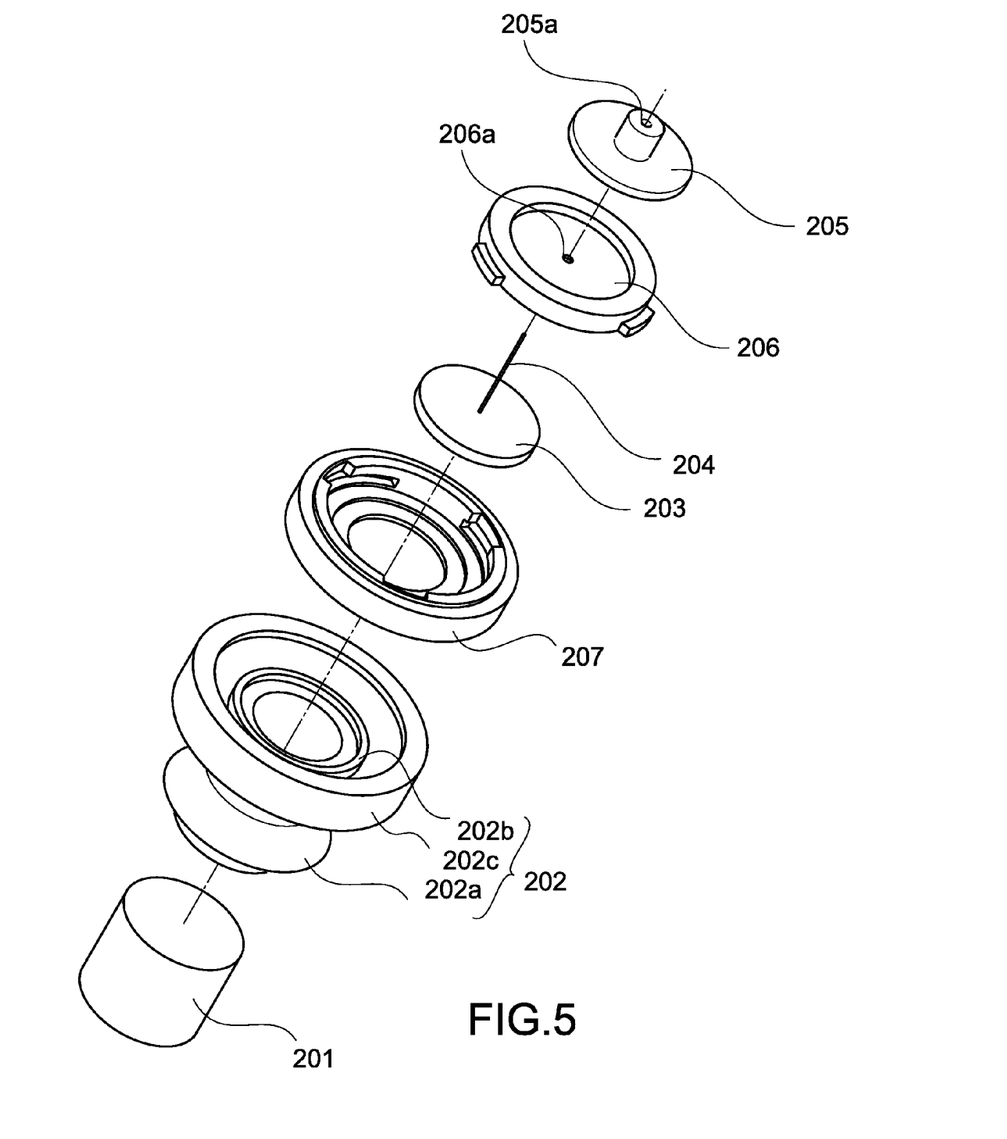
FIG. 5 is an exploded perspective view of the biosignal measurement electrode.
Figure 6:
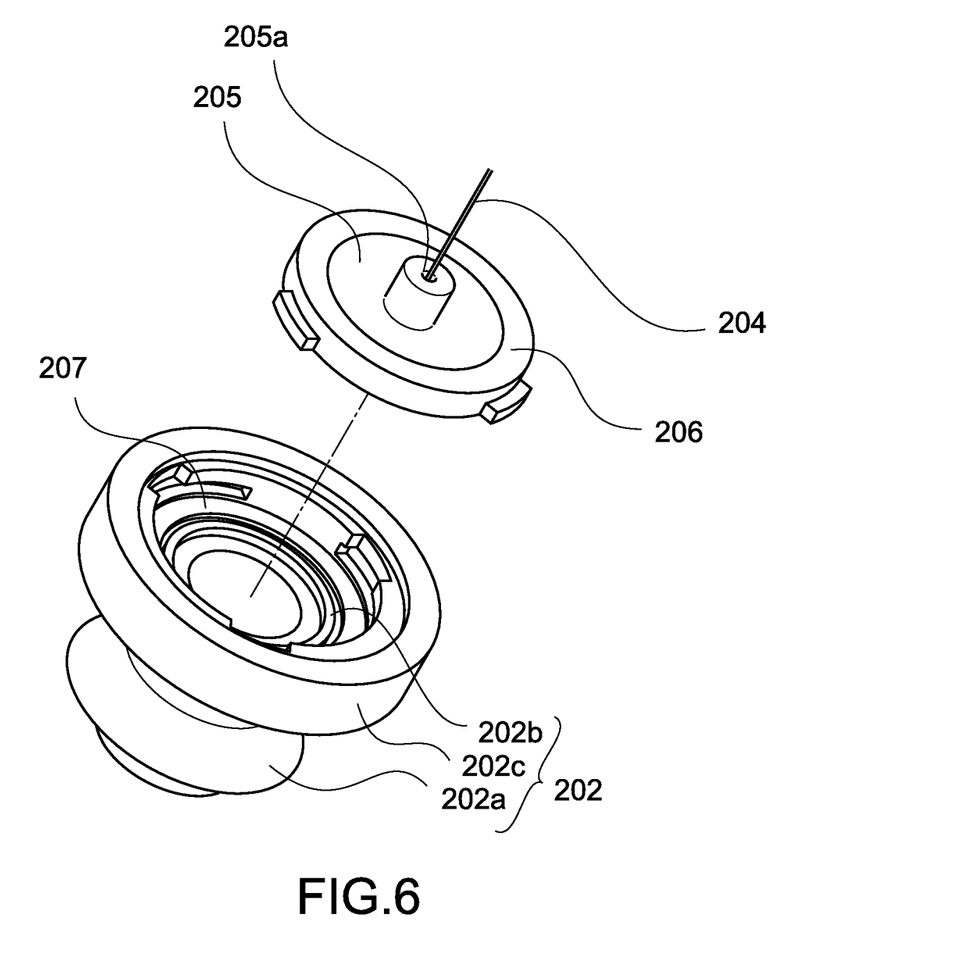
FIG. 6 is an exploded perspective view of the biosignal measurement electrode.

FIG. 4 is a cross-sectional view of the biosignal measurement electrode 200. FIGS. 5 and 6 are exploded perspective views of the biosignal measurement electrode 200. As shown in the figures, the biosignal measurement electrode 200 includes a liquid retaining member 201, a cover member 202, an electric plate 203, a wiring 204, a conductive member 205, a first insulating member 206, and a second insulating member 207.

The liquid retaining member 201 is configured to be elastically deformable and impregnated with conductive liquid. The liquid retaining member 201 may be formed of a material capable of retaining liquid and elastically deformable, such as a sponge. Further, the liquid retaining member 201 may also be formed of a gel-like material containing an electrolyte. The shape of the liquid retaining member 201 may be a circular column shape. However, the shape of the liquid retaining member 201 is not limited thereto, and various shapes such as a prism shape and semicircular shape may also be possible. Alternatively, a plurality of liquid retaining members 201 may be provided.

As shown in FIG. 4, out of a surface of the liquid retaining member 201, a surface that is exposed from the cover member 202 and brought into contact with the living body surface is referred to as a contact surface 201a. Note that the contact surface 201a does not need to be a flat plate. The conductive liquid with which the liquid retaining member 201 is impregnated is not particularly limited, and may be an electrolyte solution in which an electrolyte such as salt is dissolved, ion liquid, or the like.

Figure 9:
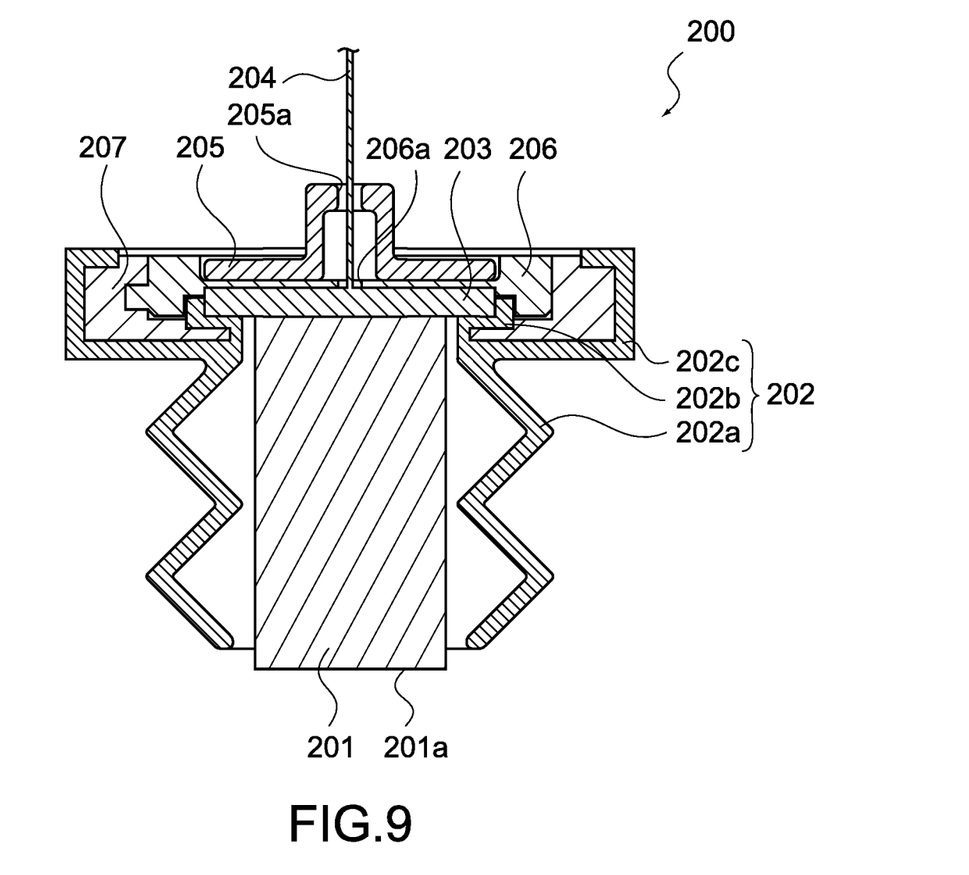
FIG. 9 is a schematic view showing a modified example of the biosignal measurement electrode.

The conductive liquid with which the liquid retaining member 201 is impregnated is brought into contact with the electric plate 203, and is conducted to the electric plate 203. As shown in FIG. 4, the liquid retaining member 201 may be brought into direct contact with the electric plate 203. In this case, when the liquid retaining member 201 is pressed, the conductive liquid is wept from the liquid retaining member 201, and is conducted to the electric plate 203. Further, as shown in FIG. 9, the liquid retaining member 201 may also be brought into direct contact with the electric plate 203.

Figure 7:
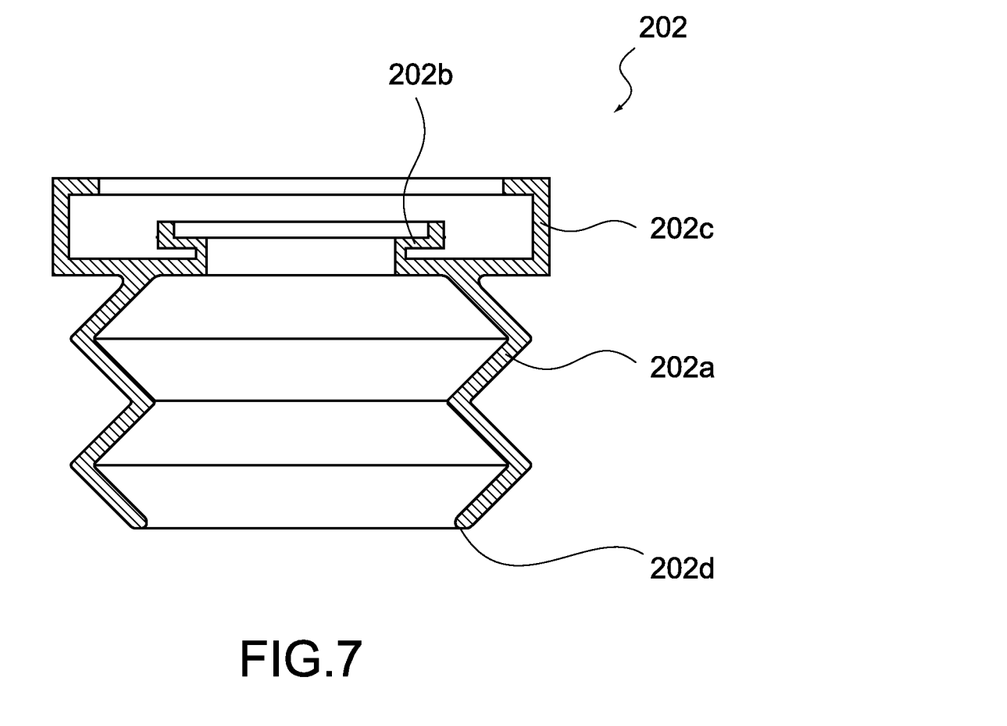
FIG. 7 is a cross-sectional view of a cover member of the biosignal measurement electrode.

The cover member 202 covers the liquid retaining member 201 except for the contact surface 201a. FIG. 7 is a cross-sectional view showing the cover member 202. As shown in the figure, the cover member 202 may include a cover portion 202a, a sealing portion 202b, and an engagement portion 202c.

The cover portion 202a is a portion covering the liquid retaining member 201 and configured to be elastically deformable. The cover portion 202a has a tubular shape having an opening 202d for exposing the contact surface 201a. Specifically, the cover portion 202a may be formed in a bellows shape with a direction perpendicular to the contact surface 201a being expansion and contraction directions (to be described later). Further, the cover portion 202a is not limited to the bellows shape, and may also be a cylindrical shape or a taper tubular shape.

As shown in FIG. 4, the cover portion 202a has a length that can cover most part of the liquid retaining member 201. Favorably, the size of the opening 202d is as small as possible as long as the cover portion 202a is not in contact with the liquid retaining member 201. That is for the purpose of effectively preventing evaporation of the conductive liquid contained in the liquid retaining member 201. Note that the cover portion 202a may have a length larger than a length of the liquid retaining member 201.

The sealing portion 202b prevents the conductive liquid with which the liquid retaining member 201 is impregnated from being brought into contact with the conductive member 205. Specifically, as shown in FIG. 4, the sealing portion 202b abuts against the electric plate 203 and can seal the conductive liquid between the sealing portion 202b and the electric plate 203 by being brought into close contact with the electric plate 203 by an elastic force. More specifically, the sealing portion 202b has an annular structure sandwiched between the second insulating member 207 and the electric plate 203 and is configured to be brought into close contact with the electric plate 203 by an elastic force against the second insulating member 207 and the electric plate 203.

The engagement portion 202c engages to the second insulating member 207, to thereby support the cover member 202 with respect to the second insulating member 207 or the like. The structure of the engagement portion 202c is not particularly limited, and the engagement portion 202c may have any structure as long as the engagement portion 202c can support the cover member 202.

As a material of the cover member 202, a material that is deformable and does not transmit the conductive liquid (also including vapor), specifically, a silicone rubber or a nitrile rubber may be used. Alternatively, a material for the cover member 202 may be appropriately selected depending on nature of the conductive liquid (e.g., hydrophilic or lipophilic), softness necessary for the cover member 202, and the like.

The electric plate 203 is brought into contact with the conductive liquid contained in the liquid retaining member 201, and electrically conducted to the conductive liquid. The electric plate 203 may be formed of a material (difficult to undergo redox reaction), for example, silver-silver chloride (Ag—Ag/Cl) or carbon exhibiting a small potential change even if the electric plate 203 is brought into contact with the conductive liquid. The electric plate 203 is electrically connected also to the conductive member 205 via the wiring 204 connected to the electric plate 203.

With such configuration, only the electric plate 203 can be brought into contact with the conductive liquid to electrically connect the conductive liquid with the conductive member 205. When the conductive liquid is brought into contact with a conductive material (conductive member 205 or the like) other than the electric plate 203, a potential change occurs and potential change noise is caused in the acquired biosignal. Therefore, contact of the conductive liquid with the conductive material other than the electric plate 203 has to be avoided. As described above, in this embodiment, the sealing portion 202b seals the conductive liquid and such contact is prevented.

The wiring 204 is connected to the electric plate 203 to electrically connect the electric plate 203 with the conductive member 205. As shown in FIGS. 5 and 6, the wiring 204 is formed of an arbitrary conductive material. The wiring 204 is inserted into a through-hole 206a formed in the first insulating member 206 and into a through-hole 205a formed in the conductive member 205. In this manner, the wiring 204 is connected to the conductive member 205.

The conductive member 205 is electrically connected to the electric plate 203 and an outside (terminal provided to the equipment 101 or the like). Further, the conductive member 205 may also be utilized as an attachment for fixing the biosignal measurement electrode 200 to the equipment 101 (see FIG. 1). In the conductive member 205, the through-hole 205a into which the wiring 204 is inserted is formed. The conductive member 205 is prevented by the first insulating member 206 from being brought into direct contact with the electric plate 203. The conductive member 205 is electrically connected to the electric plate 203 via the wiring 204 inserted into the through-hole 205a. The conductive member 205 may be formed of an arbitrary conductive material and its shape is not particularly limited. For example, the through-hole 205a is not provided, and the wiring 204 may also be connected to the conductive member 205.

The first insulating member 206 prevents direct contact with the electric plate 203 and the conductive member 205. The first insulating member 206 can be formed of an arbitrary insulating material, for example, various synthetic resins. In the first insulating member 206, the through-hole 206a for inserting the wiring 204 thereto may be formed. Further, as shown in FIG. 4, the first insulating member 206 is fitted into the second insulating member 207 via the electric plate 203. By pressing the electric plate 203 against the sealing portion 202b, the first insulating member 206 may cause the sealing portion 202b to generate an elastic force for sealing.

The second insulating member 207 supports the first insulating member 206 and the cover member 202. The second insulating member 207 may be formed of an arbitrary insulating material, for example, various synthetic resins. As described above, the engagement portion 202c may be engaged to an outer periphery of the second insulating member 207 as described above. Further, the second insulating member 207 may sandwich the sealing portion 202b together with the electric plate 203.

The biosignal measurement electrode 200 has the above-mentioned configuration.

[Operation of Biosignal Measurement Electrode]

Figure 8A:
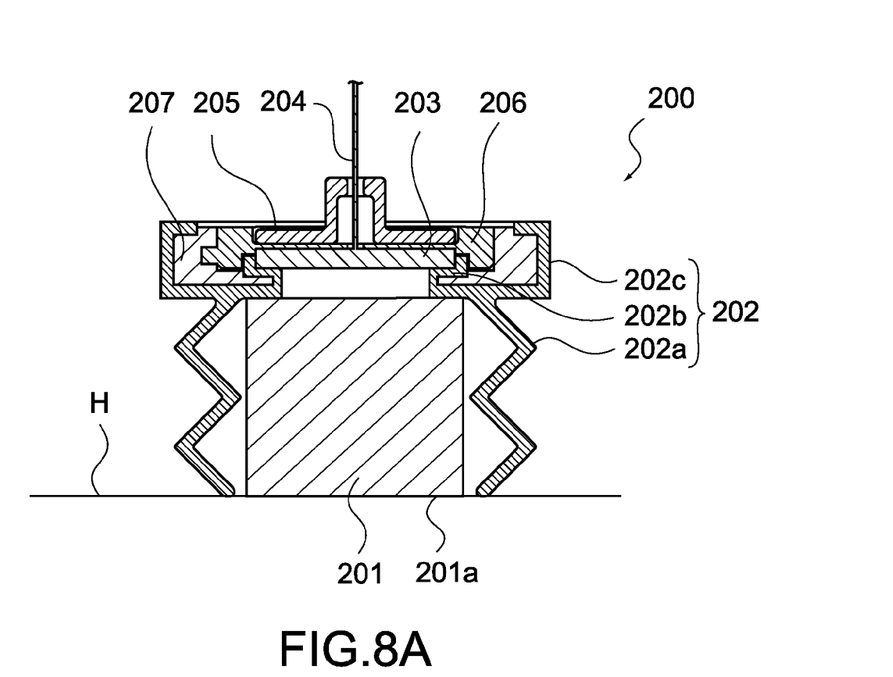
FIGS. 8A and 8B are schematic views each showing an operation of the biosignal measurement electrode.
Figure 8B:
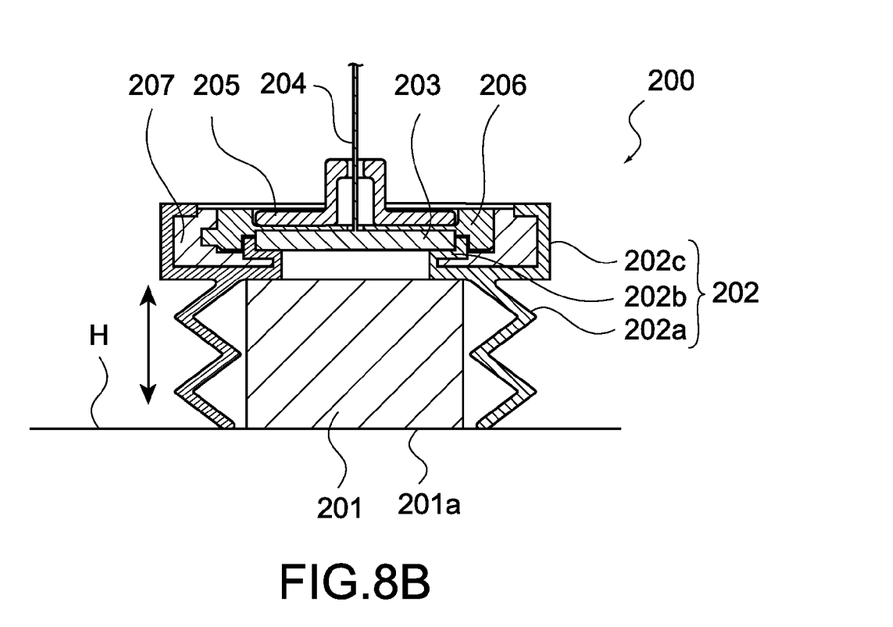

FIGS. 8A and 8B are schematic views each showing an operation of the biosignal measurement electrode 200. In FIGS. 8A and 8B, the living body surface is shown as a living body surface H. The living body surface H is a head surface of the subject U, for example. Note that, although not shown in FIGS. 8A and 8B, it is assumed that the biosignal measurement electrode 200 is attached to the equipment 101.

FIG. 8A shows a state in which the biosignal measurement electrode 200 is pressed against the living body surface H with a little pressing force. In this state, the liquid retaining member 201 is slightly deformed. The living body surface H and the conductive member 205 are electrically connected to each other via the conductive liquid with which the liquid retaining member 201 is impregnated. In this manner, biosignals are acquired.

From the state shown in FIG. 8A, when the biosignal measurement electrode 200 is pressed against the living body surface H with a larger pressing force, the liquid retaining member 201 and (cover portion 202a of) the cover member 202 are pressed against the living body surface. Thus, as shown in FIG. 8B, the liquid retaining member 201 and the cover member 202 are elastically deformed. The cover portion 202a has expansion and contraction directions in a direction perpendicular to the contact surface 201a (shown by arrows of FIG. 8B). Even if the biosignal measurement electrode 200 is tilted with respect to the living body surface H, the liquid retaining member 201 and the cover portion 202a are elastically deformed following the living body surface H.

The liquid retaining member 201 and the cover portion 202a are elastically deformed in this manner. Therefore, even if the biosignal measurement electrode 200 is pressed against the living body surface H, a pressing force is absorbed and pain is not produced in the living body surface H. Further, even if the equipment 101 causes a vibration (vibration in direction perpendicular to living body surface H and vibration in direction parallel to living body surface H) with respect to the living body surface H, the contact surface 201a maintains a contact position with respect to the living body surface H. Thus, it is possible to continuously acquire the biosignals.

In addition, the cover portion 202a is always held in contact with the living body surface H while the biosignal measurement electrode 200 is pressed against the living body surface H. With this, the cover portion 202a seals a space enclosing the liquid retaining member 201 together with the living body surface H. Thus, it is possible to prevent evaporation of the conductive liquid with which the liquid retaining member 201 is impregnated. The evaporation prevention effect of the conductive liquid is made more effective when the cover member 202 is formed of a material not transmitting the conductive liquid.

As described above, the biosignal measurement electrode 200 and the biosignal measurement apparatus 100 including the biosignal measurement electrode 200 according to this embodiment can continue acquiring the biosignals, without producing pain due to the biosignal measurement electrode 200 being pressed against the living body surface, also in the case of vibration of the biosignal measurement electrode 200 with respect to the living body surface. In addition, it is possible to prevent evaporation of the conductive liquid. Therefore, the biosignal measurement electrode 200 and the biosignal measurement apparatus 100 including the biosignal measurement electrode 200 are effective for biosignal measurement, especially, for long-time biosignal measurement.

If the biosignal measurement electrode 200 and the biosignal measurement apparatus 100 including the biosignal measurement electrode 200 are utilized for brain wave measurement during sleep, it is possible to prevent a contact failure of the electrode due to pain in contact of the electrode, which interferes with sleep of the subject, or due to movement of the body during sleep. In addition, evaporation of the conductive liquid by long-time measurement can be suppressed. Further, in the brain wave measurement, the biosignal measurement electrode 200 may be placed on the occipital region of the subject (e.g., Pz measurement electrode 102d in FIG. 1). Here, even if the subject lies on his or her back and a pressing force is added to the biosignal measurement electrode 200 placed on the posterior region due to a pillow or the like, pain due to the electrode can be prevented from being produced.

The present disclosure is not limited only to the above-mentioned embodiment and may be changed without departing from the gist of the present disclosure.

It should be noted that the present disclosure may also take the following configurations.

(1) A biosignal measurement electrode, including:
a liquid retaining member configured to be elastically deformed and impregnated with conductive liquid, the liquid retaining member including a contact surface configured to be brought into contact with a living body surface;
an electric plate configured to be brought into contact with the conductive liquid; and
a cover member configured to be elastically deformed and cover the liquid retaining member except for the contact surface.

(2) The biosignal measurement electrode according to Item (1), in which the cover member is formed of a material not transmitting the conductive liquid.

(3) The biosignal measurement electrode according to Item (1) or (2), further including
a conductive member configured to be connected to the electric plate, in which
the cover member prevents contact of the conductive liquid with the conductive member.

(4) The biosignal measurement electrode according to any one of Items (1) to (3), in which
the cover member is brought into close contact with the electric plate, to thereby seal the conductive liquid by an elastic force thereof.

(5) The biosignal measurement electrode according to any one of Items (1) to (4), in which
the cover member has a bellows shape with a direction perpendicular to the contact surface being expansion and contraction directions.

(6) A biosignal measurement apparatus, including:
a biosignal measurement electrode including
a liquid retaining member configured to be elastically deformed and retain conductive liquid, the liquid retaining member including a contact surface configured to be brought into contact with a living body surface,
an electric plate configured to be brought into the conductive liquid, and
a cover member configured to be elastically deformed and cover the liquid retaining member except for the contact surface; and
equipment configured to support the biosignal measurement electrode and cause the biosignal measurement electrode to abut against the living body surface.

(7) The biosignal measurement apparatus according to Item (6), in which
the equipment is configured to cause the biosignal measurement electrode to abut against a head of a subject, and
the biosignal measurement electrode is configured to acquire a brain wave of the subject.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A biosignal measurement electrode, comprising:
a liquid retaining member configured to be elastically deformed and impregnated with conductive liquid, the liquid retaining member including a contact surface configured to be brought into contact with a living body surface;
an electric plate configured to be brought into contact with the conductive liquid; and
a cover member configured to be elastically deformed and cover the liquid retaining member except for the contact surface,
wherein the cover member comprises:
a sealing portion having an annular structure, wherein the sealing portion abuts against the electrical plate to seal the conductive liquid between the sealing portion and the electrical plate, and
a cover portion covering the liquid retaining member and having a bellows shape along the length of the liquid retaining member in a direction perpendicular to the contact surface.

2. The biosignal measurement electrode according to claim 1, wherein the cover member is formed of a material not transmitting the conductive liquid.

3. The biosignal measurement electrode according to claim 1, further comprising a conductive member configured to be connected to the electric plate, wherein the sealing portion of the cover member prevents contact of the conductive liquid with the conductive member.

4. The biosignal measurement electrode according to claim 3, further comprising a wiring configured to connect the electric plate with the conductive member.

5. The biosignal measurement electrode according to claim 1, wherein the sealing portion of the cover member is brought into contact with the electric plate by an elastic force.

6. The biosignal measurement electrode according to claim 1, wherein the cover member further comprises an engagement portion engaged to an outer periphery of an insulating member provided between the electric plate and the cover member.

7. The biosignal measurement electrode according to claim 6, wherein the engagement portion is configured to provide support to the cover member with respect to the insulating member.

8. The biosignal measurement electrode according to claim 1, wherein a length of the cover member is larger than a length of the liquid retaining member.

9. A biosignal measurement apparatus, comprising:
a biosignal measurement electrode including:
a liquid retaining member configured to be elastically deformed and retain conductive liquid, the liquid retaining member including a contact surface configured to be brought into contact with a living body surface,
an electric plate configured to be brought into the conductive liquid, and
a cover member configured to be elastically deformed and cover the liquid retaining member except for the contact surface, wherein the cover member comprises:
a sealing portion having an annular structure, wherein the sealing portion abuts against the electric plate to seal the conductive liquid between the sealing portion and the electric plate, and
a cover portion covering the liquid retaining member and having a bellows shape along the length of the liquid retaining member in a direction perpendicular to the contact surface; and equipment configured to support the biosignal measurement electrode and cause the biosignal measurement electrode to abut against the living body surface.

10. The biosignal measurement apparatus according to claim 9, wherein the equipment is configured to cause the biosignal measurement electrode to abut against a head of a subject, and the biosignal measurement electrode is configured to acquire a brain wave of the subject.

11. A biosignal measurement electrode, comprising:

a liquid retaining member configured to be elastically deformed and impregnated with conductive liquid, the liquid retaining member including a contact surface configured to be brought into contact with a living body surface;

an electric plate configured to be brought into contact with the conductive liquid; and a cover member configured to be elastically deformed and cover the liquid retaining member except for the contact surface, wherein the cover member comprises:

a sealing portion having an annular structure, wherein the sealing portion abuts against the electric plate to seal the conductive liquid between the sealing portion and the electric plate, and a cover portion covering the liquid retaining member and having a bellows shape along the length of the liquid retaining member in a direction perpendicular to the contact surface, wherein the direction perpendicular to the contact surface corresponds to expansion and contraction directions of the cover portion.

* * * * *